United States Patent
Nomura et al.

(10) Patent No.: US 7,282,219 B2
(45) Date of Patent: Oct. 16, 2007

(54) POWDERY PREPARATION FOR TRANSMUCOSAL ADMINISTRATION CONTAINING A POLYMERIC FORM OF DRUG AND EXHIBITING IMPROVED STORAGE STABILITY

(75) Inventors: Hideaki Nomura, Gunma (JP); Yosuke Ueki, Gunma (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 662 days.

(21) Appl. No.: 10/239,694

(22) PCT Filed: Mar. 28, 2001

(86) PCT No.: PCT/JP01/02555

§ 371 (c)(1),
(2), (4) Date: Sep. 25, 2002

(87) PCT Pub. No.: WO01/74397

PCT Pub. Date: Oct. 11, 2001

(65) Prior Publication Data

US 2005/0037084 A1 Feb. 17, 2005

(30) Foreign Application Priority Data

Mar. 31, 2000 (JP) ................. 2000-99213

(51) Int. Cl.
*A61K 9/14* (2006.01)
(52) U.S. Cl. .................................... 424/489
(58) Field of Classification Search ............... 424/434, 424/408, 435, 430, 427, 134.1, 1.69, 489, 424/491, 499
See application file for complete search history.

(56) References Cited

U.S. PATENT DOCUMENTS

| | | | |
|---|---|---|---|
| 5,399,670 A | 3/1995 | Bhattacharya et al. | |
| 5,442,043 A * | 8/1995 | Fukuta et al. | 530/303 |
| 5,611,971 A * | 3/1997 | Maedera et al. | 264/4.1 |
| 5,919,443 A | 7/1999 | Michaelis et al. | |
| 5,942,253 A | 8/1999 | Gombotz et al. | |
| 6,045,830 A * | 4/2000 | Igari et al. | 424/501 |
| 6,235,481 B1 * | 5/2001 | Horikawa et al. | 435/6 |
| 6,248,363 B1 * | 6/2001 | Patel et al. | 424/497 |
| 6,294,199 B1 * | 9/2001 | Conley et al. | 424/468 |
| 6,419,961 B1 * | 7/2002 | Igari et al. | 424/501 |
| 2005/0271728 A1* | 12/2005 | Nomura et al. | 424/487 |

FOREIGN PATENT DOCUMENTS

| | | | |
|---|---|---|---|
| EP | 228862 A2 | | 7/1987 |
| EP | 0 459 516 A | | 12/1991 |
| EP | 1 093 818 | * | 1/1999 |
| EP | 0 228 862 A2 | | 7/2004 |
| JP | 60-169428 | | 9/1985 |
| JP | 60-169428 A | | 9/1985 |
| WO | WO99/10011 A | | 3/1999 |
| WO | WO 00/02574 A1 | | 1/2000 |

OTHER PUBLICATIONS

Supplementary Partial European Search Report of EP 01 91 7538.
"Bio Industry and Pharmaceutical Industry (vol. II) Pharmaceutical Industry", Jan. 1989, Published by Kyushu Tosho Bunbutu K.K., Taiwan ROC; p. 186.

* cited by examiner

*Primary Examiner*—Sharon E. Kennedy
(74) *Attorney, Agent, or Firm*—Foley & Lardner LLP

(57) ABSTRACT

A powdery preparation for transmucosal administration comprising a medicine of high molecular weight, a cationic polymer and, as needed, a viscous polymer, further comprising an effective amount of a basic amino acid. The powdery preparation for transmucosal administration has an improved storage stability for the medicine of high molecular weight while maintaining an improved mucosal absorption of the medicine.

11 Claims, No Drawings

SEQUENCE LISTING

<160> NUMBER OF SEQ ID NOS: 3

<210> SEQ ID NO 1
<211> LENGTH: 175
<212> TYPE: PRT
<213> ORGANISM: Artificial Sequence
<220> FEATURE:
<223> OTHER INFORMATION: Description of Artificial Sequence: The amino
      acid sequence comprising a Met residue at position -1 relative to
      naturally occurring human G-CSF

<400> SEQUENCE: 1

Met Thr Pro Leu Gly Pro Ala Ser Ser Leu Pro Gln Ser Phe Leu Leu
 -1   1               5                  10                  15

Lys Cys Leu Glu Gln Val Arg Lys Ile Gln Gly Asp Gly Ala Ala Leu
                 20                  25                  30

Gln Glu Lys Leu Cys Ala Thr Tyr Lys Leu Cys His Pro Glu Glu Leu
             35                  40                  45

Val Leu Leu Gly His Ser Leu Gly Ile Pro Trp Ala Pro Leu Ser Ser
         50                  55                  60

Cys Pro Ser Gln Ala Leu Gln Leu Ala Gly Cys Leu Ser Gln Leu His
     65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
    145                 150                 155

Phe Leu Glu Val Ser Tyr Arg Val Leu Arg His Leu Ala Gln Pro
160                 165                 170

<210> SEQ ID NO 2
<211> LENGTH: 174
<212> TYPE: PRT
<213> ORGANISM: Homo sapiens
<220> FEATURE:
<223> OTHER INFORMATION: The amino acid sequence of naturally occurring
      human G-CSF

<400> SEQUENCE: 2

Thr Pro Leu Gly Pro Ala Ser Ser Leu Pro Gln Ser Phe Leu Leu Lys
  1               5                  10                  15

```
Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 3
<211> LENGTH: 175
<212> TYPE: PRT
<213> ORGANISM: Artificial Sequence
<220> FEATURE:
<223> OTHER INFORMATION: Description of Artificial Sequence: The amino
      acid sequence comprising a Met reside at position -1, including
      various residue substitutions according to the application as
      filed, relative to naturally occurring human G-CSF

<400> SEQUENCE: 3

```
Met Ala Pro Thr Tyr Arg Ala Ser Ser Leu Pro Gln Ser Phe Leu Leu
-1   1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
    145                 150                 155

Phe Leu Glu Val Ser Tyr Arg Val Leu Arg His Leu Ala Gln Pro
160                 165                 170
```

POWDERY PREPARATION FOR TRANSMUCOSAL ADMINISTRATION CONTAINING A POLYMERIC FORM OF DRUG AND EXHIBITING IMPROVED STORAGE STABILITY

TECHNICAL FIELD

The present invention relates to a powdery preparation for transmucosal administration comprising a medicine of high molecular weight and a cationic polymer, the preparation further comprising a basic amino acid and exhibiting an improved storage stability. Particularly, the invention relates to such a preparation for administration through the nasal mucosa.

BACKGROUND ART

Currently, medicines of high molecular weight are administered by an intravenous or subcutaneous injection for treatment. Administration of medicines of high molecular weight by injection is difficult for patients to perform by themselves and is accompanied by pain. It is hoped, therefore, to employ transmucosal administration as an alternative and easier method of administration. Examples of transmucosal administration include administration through the mucosa of digestive tracts such as the stomach, small intestine, large intestine, and rectum, as well as the nose, eye, mouth, lung, and vagina. Administration through the nasal mucosa, among others, is gaining attention as a relatively easy method of administration, which allows for quick absorption of the drug and reliable effects.

The applicant has found that the difficulty associated with absorption of a medicine of high molecular weight, contained in a powdery preparation for transmucosal administration and absorbed through mucosa, can be significantly reduced by providing the medicine of high molecular weight with a cationic polymer (and additionally a viscous polymer, if necessary) (International Application No.: WO 00/02574).

The applicant has since made a continuous effort to find ways of improving the storage stability of the preparation.

It is therefore an object of the present invention to provide a powdery preparation for transmucosal administration comprising a medicine of high molecular weight and a cationic polymer in which the storage stability of the medicine of high molecular weight is improved while maintaining the improved transmucosal absorption of the medicine of high molecular weight.

SUMMARY OF THE INVENTION

The present invention is based on the inventors' realization that, in a powdery preparation for transmucosal administration comprising a medicine of high molecular weight and a cationic polymer with an improved mucosal absorption, as described in the International Application No.: WO 00/02574, the storage stability of the medicine can be significantly and unexpectedly improved by adding an effective amount of basic amino acid.

The present invention can be summarized as follows.

The present invention, in its various embodiments, provides a powdery preparation for transmucosal administration comprising one or more medicines of high molecular weight and one or more cationic polymers with an improved storage stability, wherein the preparation further comprising at least one type of basic amino acid or its pharmaceutically acceptable salt.

In a first embodiment of the present invention, the basic amino acid or its salt is optically active or inactive histidine, arginine, lysine, a pharmaceutically acceptable salt thereof, or a derivative thereof. The basic amino acid or its salt is preferably optically active or inactive histidine, arginine, or a pharmaceutically acceptable salt thereof, and is more preferably optically active or inactive histidine or a pharmaceutically acceptable salt thereof.

As used herein, "optically active" refers to the properties of a chiral structure. An optically active substance normally has a three-dimensional D- or L-, or S- or R-configuration. On the other hand, "optically inactive" refers to the properties of an achiral structure.

In a second embodiment of the present invention, the improved storage stability is characterized by the content (according to HPLC analysis) of the medicine of high molecular weight of not less than 93%, preferably not less than 96%, against the value of 100% at the initial point in a storage stability test of 50° C. for two weeks.

In a third embodiment of the present invention, the cationic polymer is selected from the group consisting of aminoalkyl methacrylate copolymer, polyvinylacetal diethylaminoacetate, and poly-L-arginine. Preferably, the cationic polymer is either aminoalkyl methacrylate copolymer or polyvinylacetal diethylaminoacetate. More preferably, the cationic polymer is aminoalkyl methacrylate copolymer.

As used herein, "cationic polymer" refers to a polymer having such a structure where a cationic charge is present in a fundamental unit making up a repetitive structure, or where a cationic charge comes into existence in the fundamental unit when the polymer is dissolved.

In a fourth embodiment of the present invention, the preparation further comprises one or more viscous polymers. The viscous polymer refers to a polymer which exhibits a viscosity when dissolved or swelled. Hydroxypropyl methylcellulose is an example of such polymer.

In a fifth embodiment of the present invention, the medicine of high molecular weight is physiologically active peptide or protein (including antibody, vaccine and antigen). Specific examples include, but are not limited to, granulocyte colony-stimulating factor, insulin, erythropoietin, growth hormone, and influenza antigen.

In a sixth embodiment of the present invention, the preparation is adapted for transnasal administration.

In a seventh embodiment of the present invention, the preparation further comprises one or more excipients. The excipient refers to a substance that is added to the formula in order to impart proper hardness and shape during the manufacture of drugs.

This specification includes part or all of the contents as disclosed in the specification of Japanese Patent Application No. 2000-99213, which is a priority document of the present application.

DETAILED DESCRIPTION OF THE INVENTION

The present invention will be hereafter described in detail.

The powdery preparation for transmucosal administration according to the present invention can be obtained by adding to a medicine of high molecular weight an excipient, a cationic polymer and basic amino acid or its salt, and further a viscous polymer as needed, and additionally an appropriate additive as needed, and then freeze-drying or spray-drying the mixture.

As used herein, the medicine of high molecular weight refers to a bioactive peptide and protein (including antibodies, vaccines, and antigens). Examples of the medicine of high molecular weight include, but are not limited to: calcitonin, insulin, proinsulin, vasopressin, desmopressin, luteinizing hormone, luteinizing hormone-releasing hormone, somatostatin, prolactin, glucagon, gastrin, secretin, kallikrein, urokinase, neurotensin, enkephalin, kyotorphin, endorphin, endothelin, angiotensin, transferrin, atrial natriuretic peptide, epidermal growth factor, growth hormone, parathyroid hormone, interferon, interleukin, tumor necrosis factor, leukemic cell inhibiting factor, blood stem cell growth factor, erythropoietin, granulocyte colony-stimulating factor (G-CSF), granulocyte-macrophage colony-stimulating factor, macrophage-colony stimulating factor, thrombopoietin, superoxide dismutase, tissue plasminogen activator, antithrombin, blood coagulation factor, anti-IgE antibody, anti-IgA antibody, antitumor antibody, tumor necrosis factor antibody, anti-interleukin antibody, HIV neutralizing antibody, antiplatelet antibody, anti-hepatitis virus antibody, hepatitis vaccine, influenza vaccine (influenza antigen), pertussis vaccine, diphtheria vaccine, tetanus vaccine, and peptide or protein such as cedar pollen and ragweed pollen that can function as an antigen, a conjugate of a hapten thereof, and a mixture thereof with an adjuvant. It can be readily estimated that even with medicines with smaller molecular weight than the above examples of the medicine of high molecular weight, the present invention can increase their absorption through mucous membranes, particularly nasal mucosa, and therefore the present invention is believed also useful in applications with a medicine of low-molecular weight.

Examples of the G-CSF, which is one of the medicines of high molecular weight that can be used in the present invention, include a protein with a human G-CSF activity represented by amino acid sequences of SEQ ID NOS: 1-3, or a glycoprotein in which one or more sugar chains are attached to the protein. The G-CSF according to the present invention further includes G-CSF derivatives with G-CSF activity in which part of the above amino acid sequences has been modified (i.e., by substitution, deletion, insertion and/or addition of one or more amino acid residues). These G-CSFs can be extracted, separated and purified from naturally occurring materials, or they can be produced by a transformant obtained by transforming a host cell by genetic engineering, and then isolated and purified. Examples of the host cell include *Escherichia coli* and mammalian cells (such as C127 and CHO cells). The detailed methods of manufacturing them are known from, e.g., Japanese Patent Application Laid-Open (Kohyo) No. 63-500636, Japanese Patent Application Laid-Open (Kokai) Nos. 62-236497, 62-236488, and 63-267292, and these known methods can be employed in the present invention.

The content of the medicine of high molecular weight in the powdery preparation for transmucosal administration according to the present invention is normally in the range of from 0.01 to 90 W/W %, preferably from 0.1 to 50 W/W %. As used herein, W/W % refers to the ratio (weight %) of the additive component relative to the entire weight of the preparation.

As used herein, the cationic polymer refers to a polymer with a structure such that a cation charge is present in a fundamental unit making up a repetitive structure, or such that a cation charge comes into existence in the fundamental unit when the polymer is dissolved. The cationic polymer used in the present invention is not limited to any particular polymer as long as it can provide the effect of facilitating the absorption of the medicine of high molecular weight through mucous membrane. Concrete examples include aminoalkyl methacrylate copolymer, polyvinylacetal diethylaminoacetate, and poly-L-arginine. Aminoalkyl methacrylate copolymers are available from, e.g., Rohm Pharma under the trade names Eudragit E and Eudragit RS. Eudragit E is a copolymer of methyl methacrylate, butyl methacrylate and dimethylaminoethyl methacrylate, with an average molecular weight of 150,000. Polyvinylacetal diethylaminoacetate is available from, e.g., Sankyo (K.K.) under the trade name AEA. This is a copolymer in which acetal compound obtained by dehydration of polyvinyl alcohol and acetaldehyde, and diethyl amino acetic acid are joined via part of hydroxyl groups of the acetal compound to form ester linkage, with an average molecular weight of 65,000. Poly-L-arginine is a copolymer of L-arginine, and it may have an average molecular weight ranging from 1,000 to 1,000,000, preferably from 12,100 to 92,000, and more preferably 92,000. Poly-L-arginine is available from Sigma Chemical Co. The content of the cationic polymer in the powdery preparation for transmucosal administration according to the present invention is normally in the range of from 0.1 to 90 W/W %, preferably from 1 to 50 W/W %.

As used herein, the basic amino acid is as defined above. Concrete examples include L- or D-, S- or R- , and DL-histidine, arginine and lysine, a pharmaceutically acceptable salt thereof, and a derivative thereof. Examples of the pharmaceutically acceptable salt include salts with inorganic acids such as hydrochloric acid, sulfuric acid and phosphoric acid, and salts with organic acids such as acetic acid, butyric acid, succinic acid, tartaric acid, citric acid, and malic acid. Examples of the derivative include methylhistidine, histidine methyl ester, acetyl histidine, acetyl lysine, hydroxylysine, and acetyllysine methyl ester. The content of the basic amino acid or its salt in the powdery preparation for transmucosal administration according to the present invention is normally in the range of from 0.1 to 10.0 W/W %, preferably from 0.5 to 5.0 W/W %. Other ranges may be used as long as they can ensure the improvement in the storage stability of the medicine of high molecular weight.

As used herein, the viscous polymer refers to a polymer that exhibits viscosity when dissolved or swelled. The viscous polymer used in the present invention may be of any type as long as it can increase, when used in combination with the cationic polymer, the absorption of the medicine of high molecular weight as compared with the case where the cationic polymer is used alone. Specific examples of such a polymer include hydroxypropyl methylcellulose, hydroxypropyl cellulose, carboxyvinyl polymer, agar powder, and gum arabic powder. The content of the viscous polymer in the powdery preparation for transmucosal administration according to the present invention is normally in the range of from 0.1 to 90 W/W %, preferably from 1 to 50 W/W %.

The excipient used in the present invention is represented by saccharides, of which examples include xylitol, fructose, sorbitol, lactose, inositol, sucrose, and mannitol. Other examples of the excipients include starches, minerals, organic acids, and amino acids. The starches include cornstarch, wheat starch, and potato starch. The minerals include calcium phosphate, calcium hydrogen phosphate, disodium hydrogen phosphate, sodium dihydrogen phosphate, magnesium carbonate, sodium chloride, and calcium sulphate. The organic acids include succinic acid, tartaric acid, citric acid, fumaric acid, malic acid, gluconic acid, glucuronic acid, and a salt thereof. The amino acids include D- and L-methionine, L-phenylalanine, and L-glutamic acid. The content of the excipient in the powdery preparation for transmucosal administration according to the present invention is normally in the range of from 1 to 90 W/W %, preferably from 5 to 80 W/W %.

In the present invention, an additive such as a lubricant may be used as needed. Examples of the lubricant include magnesium stearate, stearic acid, and talc. The content of the additive in the powdery preparation for transmucosal administration according to the present invention is normally in the range of from 0.01 to 90 W/W %, preferably from 0.05 to 50 W/W.

The powdery preparation for transmucosal administration according to the present invention may be prepared by mixing, e.g., a (buffer) solution containing a medicine of high molecular weight with a (buffer) solution in which a cationic polymer, a basic amino acid or its salt, an excipient such as sucrose and mannitol, and, if needed, a viscous polymer, have been dissolved in advance. The mixture is then spray dried to obtain a powder. A necessary amount of the obtained powder can be weighed and filled in a capsule to obtain the powdery preparation.

The powder of the preparation thus manufactured normally has a particle size (diameter) in the range of from 0.1 to 500 μm, preferably from 5 to 100 μm.

Capsulation makes the handling of the powdery preparation for transmucosal administration easy. Examples of the material for the capsule include gelatin, hydroxypropyl methylcellulose, methylcellulose, and starch. To these materials, glycerin, sorbitol, carrageenan, polyethylene glycol, gum arabic, or the like may be added, to thereby increase plasticity.

As a further additive, one or more of potassium chloride, sucrose, coloring agent, and titanium oxide may be added.

The powdery preparation for transmucosal administration according to the present invention can be administered to the patient's mucosa when needed or at proper intervals of administration. Examples of the mucosa include the mucosae of nose, eye, mouth, lung, vagina, and digestive tracts such as the stomach, small intestine, large intestine and rectum. When the preparation according to the present invention is administered through nose, for example, a capsule containing the powdery preparation may be set in a miniature spray apparatus (Pulverizer). A hole is cut in the capsule, the nozzle of the pulverizer is inserted into one or both of the nostrils, and the powdery preparation can be sprayed into the nasal cavity by squeezing the rubber ball while inhaling through nose. A preparation containing a granulocyte colony-stimulating factor as an active ingredient can be administered to a patient one to four times a day, and in the amount of the active ingredient of 1 to 500 μg/kg/day, preferably 5 to 100 μg/kg/day. A preparation containing insulin as an active ingredient can be administered to a patient one to four times a day, and in the amount of the active ingredient of 0.1 to 100 U/kg/day, preferably 0.5 to 20 U/kg/day. A preparation comprising erythropoietin as an active ingredient can be administered to a patient one to four times a day, and in the amount of the active ingredient of 50 to 50,000 IU/kg/day, preferably 200 to 8,000 IU/kg/day. A preparation comprising growth hormone as an active ingredient can be administered to a patient one to four times a day, and in the amount of the active ingredient of 0.1 to 50 IU/kg/day, preferably 0.4 to 15 IU/kg/day. A preparation comprising influenza antigen as an active ingredient can be administered to a subject one to four times a day at intervals of 2 to 6 weeks, and in the amount of the active ingredient of 0.5 to 200 CCA/kg/day, preferably 2 to 40 CCA/kg/day.

As described above, the present invention is characterized in that, in a powdery preparation for transmucosal administration comprising a medicine of high molecular weight and a cationic polymer with an improved mucosal absorption, the storage stability of the medicine of high molecular weight is improved to a practical level. In this respect, the present invention is an improvement over the invention disclosed in the applicant's International Application WO 00/02574. Accordingly, the various specific examples disclosed in the above international application are also applicable to the present invention and, therefore, all of the contents disclosed therein are incorporated in the present specification.

EXAMPLES

While the invention will be hereafter described by way of specific examples, it should be understood that the scope of the invention is not limited to these examples.

The basic amino acid, cationic polymer, sucrose, D-mannitol, hydroxypropyl methylcellulose, sodium hyaluronate, and the components of the buffer solutions (buffer components) that were used in the following examples and comparative examples, are as follows:

Basic amino acid
  L-arginine hydrochloride (Ajinomoto)
  L-histidine (Ajinomoto)
  L-lysine hydrochloride (Ajinomoto)
Cationic polymer
  Aminoalkyl methacrylate copolymer E (Rohm Pharma, trade name:
Eudragit E100)
D-mannitol (Kao, Nikkyoku Mannitol Kao)
Hydroxypropyl methylcellulose (Shin-Etsu Chemical, trade name: Metolose 60SH4000)
Buffer Components
  Citric Acid (Toyo Seiyaku Kasei), Phosphoric Acid (Kokusan Kagaku)

The granulocyte colony-stimulating factor (G-CSF) used as the medicine of high molecular weight in the following examples is a polypeptide with the amino acid sequence shown in SEQ ID NO: 1 (see Japanese Patent Application Laid-Open (Kohyo) No. 63-500636), produced by genetically modified *Escherichia coli*. The thus obtained G-CSF was concentrated and then the buffer solution was substituted, thereby obtaining a G-CSF buffer solution.

Example 1

A buffer solution of D-mannitol, L-arginine hydrochloride, hydroxypropyl methylcellulose (HPMC) and aminoalkyl methacrylate copolymer (Eudragit E100) was added to a buffer solution of granulocyte colony-stimulating factor (G-CSF). After adjusting the pH to 5.0, the mixture was spray dried to obtain a powdery preparation with the following formula:

| | |
|---|---|
| G-CSF | 2.5 W/W % |
| Eudragit E100 | 7.5 W/W % |
| HPMC | 10.0 W/W % |
| L-arginine hydrochloride | 5.0 W/W % |
| D-mannitol | 71.9 W/W % |
| Buffer components | Adequate amount |
| Total | 100.0 W/W % |

Example 2

A buffer solution of D-mannitol, L-lysine hydrochloride hydroxypropyl methylcellulose (HPMC) and aminoalkyl methacrylate copolymer (Eudragit E100) was added to a buffer solution of granulocyte colony-stimulating factor (G-CSF). After adjusting the pH to 5.0, the mixture was spray dried to obtain a powdery preparation with the following formula:

| | |
|---|---|
| G-CSF | 2.5 W/W % |
| Eudragit E100 | 7.5 W/W % |
| HPMC | 10.0 W/W % |
| L-lysine hydrochloride | 5.0 W/W % |
| D-mannitol | 71.9 W/W % |
| Buffer components | Adequate amount |
| Total | 100.0 W/W % |

Example 3

A buffer solution of D-mannitol, L-histidine, hydroxypropyl methylcellulose (HPMC) and aminoalkyl methacrylate copolymer (Eudragit E100) was added to a buffer solution of granulocyte colony-stimulating factor (G-CSF). After adjusting the pH to 5.0, the mixture was spray dried to obtain a powdery preparation with the following formula:

| | |
|---|---|
| G-CSF | 2.5 W/W % |
| Eudragit E100 | 7.5 W/W % |
| HPMC | 10.0 W/W % |
| L-histidine | 5.0 W/W % |
| D-mannitol | 70.8 W/W % |
| Buffer components | Adequate amount |
| Total | 100.0 W/W % |

Comparative Example 1

A buffer solution of D-mannitol, hydroxypropyl methylcellulose (HPMC) and aminoalkyl methacrylate copolymer (Eudragit E100) was added to a buffer solution of granulocyte colony-stimulating factor (G-CSF). After adjusting the pH to 5.0, the mixture was spray dried to obtain a powdery preparation with the following formula:

| | |
|---|---|
| G-CSF | 2.5 W/W % |
| Eudragit E100 | 7.5 W/W % |
| HPMC | 10.0 W/W % |
| D-mannitol | 75.7 W/W % |
| Buffer components | Adequate amount |
| Total | 100.0 W/W % |

Experiment 1

Tests were conducted to examine the stability of G-CSF in the spray-dried powders according to Examples 1-3 and Comparative Example 1. As the mode of packaging for the stability tests, a pillow packaging made of aluminum and containing a desiccant was employed, the pillow package housing PTP-packaged capsules filled with the powders to be tested. The storage temperature and period were 50° C. and two weeks. The G-CSF stability in the powder was evaluated on the basis of the percentage of the G-CSF peak area in the total peak area at the time of analysis by means of cationic ion exchange HPLC. Analysis conditions for the cationic ion exchange HPLC are as follows.

HPLC Analysis Conditions
Column used: Toso TSKgel SP-NPR
Mobile phase A: A solution of 20 mM acetic acid (pH=5.4)
Mobile phase B: A solution of 20 mM acetic acid and 100 mM sodium chloride (pH=5.4)
Gradient conditions

| Time (min) | Mobile phase A | Mobile phase B |
|---|---|---|
| 0 | 100% | 0% |
| 2 | 100% | 0% |
| 28 | 35% | 65% |
| 31 | 0% | 100% |
| 35 | 0% | 100% |
| 37 | 100% | 0% |
| 40 | 100% | 0% |

Table 1 shows the results of the cationic ion exchange HPLC analysis of the above seven types of powders (the values in the table are percentages of G-CSF peak areas in the total peak area). The results indicate that every one of Examples 1-3 has a better G-CSF stability than Comparative Example 1. Among these, L-arginine hydrochloride (Example 1) and L-histidine (Example 3) had an outstanding G-CSF stabilizing effect.

TABLE 1

Results of G-CSF storage stability analysis

| Powdery preparation | Example 1 | Example 2 | Example 3 | Comparative Example 1 |
|---|---|---|---|---|
| At Initial Point | 98.6% | 98.4% | 98.4% | 98.8% |
| After 2 weeks at 50° C. | 93.5% | 91.5% | 94.9% | 85.9% |

Example 4

A buffer solution of D-mannitol, L-histidine, hydroxypropyl methylcellulose (HPMC) and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| | |
|---|---|
| G-CSF | 2.5 W/W % |
| Eudragit E100 | 5.0 W/W % |
| HPMC | 5.0 W/W % |
| L-histidine | 0.5 W/W % |
| D-mannitol | 85.3 W/W % |
| Buffer components | Adequate amount |
| Total | 100.0 W/W % |

Example 5

A buffer solution of D-mannitol, L-histidine, hydroxypropyl methylcellulose (HPMC) and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| G-CSF | 2.5 W/W % |
|---|---|
| Eudragit E100 | 5.0 W/W % |
| HPMC | 5.0 W/W % |
| L-histidine | 1.0 W/W % |
| D-mannitol | 84.5 W/W % |
| Buffer components | Adequate amount |
| Total | 100.0 W/W % |

Example 6

A buffer solution of D-mannitol, L-histidine, hydroxypropyl methylcellulose (HPMC) and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| G-CSF | 2.5 W/W % |
|---|---|
| Eudragit E100 | 5.0 W/W % |
| HPMC | 5.0 W/W % |
| L-histidine | 2.0 W/W % |
| D-mannitol | 83.4 W/W % |
| Buffer components | Adequate amount |
| Total | 100.0 W/W % |

Example 7

A buffer solution of D-mannitol, L-histidine, hydroxypropyl methylcellulose (HPMC) and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| G-CSF | 2.5 W/W % |
|---|---|
| Eudragit E100 | 5.0 W/W % |
| HPMC | 5.0 W/W % |
| L-histidine | 5.0 W/W % |
| D-mannitol | 79.7 W/W % |
| Buffer components | Adequate amount |
| Total | 100.0 W/W % |

Comparative Example 2

A buffer solution of D-mannitol, hydroxypropyl methylcellulose (HPMC) and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| G-CSF | 2.5 W/W % |
|---|---|
| Eudragit E100 | 5.0 W/W % |
| HPMC | 5.0 W/W % |
| D-mannitol | 85.5 W/W % |
| Buffer components | Adequate amount |
| Total | 100.0 W/W % |

Experiment 2

Tests were conducted to examine the stability of G-CSF in the spray-dried powders according to Examples 4-7 and Comparative Example 2. As the mode of packaging for the stability tests, a pillow packaging made of aluminum and containing a desiccant was used, the pillow package housing PTP-packaged capsules filled with the powders to be tested. The storage temperature and period were 50° C. and two weeks. The G-CSF stability in the powders was evaluated on the basis of the percentage of the G-CSF peak area in the total peak area at the time of analysis by means of cationic ion exchange HPLC. The cationic ion exchange HPLC was conducted under the same conditions as in Experiment 1.

Table 2 shows the results of the cationic ion exchange HPLC analysis of the above five types of powders (the values in the table are the percentages of the G-CSF peak area in the total peak area). The results indicate that every one of Examples 4-7 has an improved G-CSF stability as compared with Comparative Example 2, which does not contain L-histidine. The results also indicate that G-CSF stability tends to increase with an increasing amount of L-histidine added.

TABLE 2

Results of G-CSF storage stability analysis

| Powdery preparation | Example 4 | Example 5 | Example 6 | Example 7 | Comparative Example 2 |
|---|---|---|---|---|---|
| At Initial Point | 97.2% | 96.8% | 96.9% | 96.5% | 95.6% |
| After 2 weeks at 50° C. | 91.8% | 92.7% | 93.1% | 93.6% | 87.3% |

Example 8

A buffer solution of D-mannitol, L-histidine, and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| G-CSF | 10.0 W/W % |
|---|---|
| Eudragit E100 | 5.0 W/W % |
| L-histidine | 1.0 W/W % |
| D-mannitol | 79.8 W/W % |
| Buffer components | Adequate amount |
| Total | 100.0 W/W % |

Example 9

A buffer solution of D-mannitol, L-histidine, and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| | |
|---|---|
| G-CSF | 10.0 W/W % |
| Eudragit E100 | 5.0 W/W % |
| L-histidine | 2.0 W/W % |
| D-mannitol | 78.8 W/W % |
| Buffer components | Adequate amount |
| Total | 100.0 W/W % |

Example 10

A buffer solution of D-mannitol, L-histidine, and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| | |
|---|---|
| G-CSF | 10.0 W/W % |
| Eudragit E100 | 5.0 W/W % |
| L-histidine | 5.0 W/W % |
| D-mannitol | 75.8 W/W % |
| Buffer components | Adequate amount |
| Total | 100.0 W/W % |

Comparative Example 3

A buffer solution of D-mannitol and aminoalkyl methacrylate copolymer (Eudragit E100) was added to a buffer solution of granulocyte colony-stimulating factor (G-CSF). After adjusting the pH to 4.0, the mixture was spray dried to obtain a powdery preparation with the following formula:

| | |
|---|---|
| G-CSF | 10.0 W/W % |
| Eudragit E100 | 5.0 W/W % |
| D-mannitol | 80.8 W/W % |
| Buffer components | Adequate amount |
| Total | 100.0 W/W % |

Experiment 3

Tests were conducted to examine the stability of G-CSF in the spray-dried powders according to Examples 8-10 and Comparative Example 3. As the mode of packaging for the stability tests, a pillow packaging made of aluminum and containing a desiccant was used, the pillow package housing PTP-packaged capsules filled with the powders to be tested. The test temperature and period were 50° C. and two weeks. The G-CSF stability in the powders was evaluated on the basis of the percentage of the impurity peak area in the total peak area at the time of analysis by means of reverse-phase HPLC and gel filtration HPLC. Analysis conditions for reverse-phase HPLC and gel filtration HPLC are as follows.

Reverse-phase HPLC Analysis Conditions

Column used: ChemcoPak NUCLEOSIL 300-10C8 4 (4.6 mmID×25 cm)

Mobile phase A: 30% 1-propanol, and 0.1% trifluoroacetic acid

Mobile phase B: 80% 1-propanol, and 0.1% trifluoroacetic acid

Gradient conditions

| Time (min) | Mobile phase A | Mobile phase B |
|---|---|---|
| 0 | 90% | 10% |
| 2 | 90% | 10% |
| 13 | 70% | 30% |
| 15 | 0% | 100% |
| 18 | 0% | 100% |
| 20 | 90% | 10% |

Gel filtration HPLC analysis conditions

Column used: TSK-GEL G3000SW (7.5 mm ID×60 cm)

Mobile phase: A solution of 10 mM acetic acid, 0.58% sodium chloride, and 0.3% sodium dodecyl sulfate (pH=5.5)

Tables 3 and 4 show the results of the reverse-phase HPLC analysis and gel filtration HPLC analysis of the above four types of powders (the values in the tables are percentages of the impurity peak area in the total peak area). The results indicate that in all of Examples 8-10, the G-CSF Stability is improved over Comparative Example 3, which does not contain L-histidine. The results also indicate that the increase in the amount of L-histidine added tends to prevent the increase in the amount of impurities after two weeks at 50° C., although this increases somewhat the amount of impurities at the initial point.

TABLE 3

Results of analysis by reverse-phase HPLC

| Powdery preparation | Example 8 | Example 9 | Example 10 | Comparative Example 3 |
|---|---|---|---|---|
| At Initial Point | 0.96% | 1.08% | 1.15% | 1.22% |
| After 2 weeks at 50° C. | 1.85% | 1.78% | 1.51% | 2.49% |

TABLE 4

Results of analysis by gel filtration HPLC

| Powdery preparation | Example 8 | Example 9 | Example 10 | Comparative Example 3 |
|---|---|---|---|---|
| At Initial Point | 0.93% | 0.97% | 1.36% | 1.30% |
| After 2 weeks at 50° C. | 1.52% | 1.41% | 1.29% | 2.34% |

INDUSTRIAL APPLICABILITY

In accordance with the present invention, an effective amount of basic amino acid is added to a powdery preparation for transmucosal administration comprising a medicine of high molecular weight and a cationic polymer (particularly, aminoalkyl methacrylate copolymer or polyvinylacetal diethylaminoacetate). This improves the storage stability of the medicine of high molecular weight in the preparation significantly and up to a practical level, while allowing the medicine of high molecular weight to be effectively absorbed through mucosa.

Sequence Listing Free Text

SEQ ID NO: 1 Description of an artificial sequence: An amino acid sequence comprising a Met residue at −1 position of naturally occurring human G-CSF.

SEQ ID NO: 2 Description of a sequence: An amino acid sequence of naturally occurring human G-CSF.

SEQ ID NO: 3 Description of an artificial sequence: An amino acid sequence comprising a Met residue at −1 position of natural human G-CSF, further comprising Ala, Thr, Tyr, Arg, and Ser residues substituted for Thr residue at +1 position, Leu residue at +3 position, Gly residue at +4 position, Pro residue at +5 position, and Cys residue at +17 position, respectively.

All publications, patents and patent applications cited herein are incorporated herein by reference in their entity. It is to be understood that while various changes and modifications may be made without departing from the spirit and scope of the present invention as set out in the accompanying claims, such changes and modifications within the range of equivalence are intended to be within the scope of the invention.

The invention claimed is:

1. A powdery preparation for transmucosal administration with an improved storage stability, comprising (i) a medicine of high molecular weight, (ii) a cationic polymer, and (iii) an effective amount of at least one basic amino acid or its pharmaceutically acceptable salt or derivative that improves the storage stability of the preparation, wherein (a) the cationic polymer is an aminoalkyl methacrylate copolymer, (b) the basic amino acid or its pharmaceutically acceptable salt or derivative thereof is an optically active or inactive histidine or arginine, and (c) the storage stability is improved so that the content of the medicine is not less than 93% when analyzed by HPLC in a storage test at 50° C. for two weeks' storage, based on the value of 100% at the initial point.

2. The preparation according to claim 1, wherein the basic amino acid or its salt is optically active or inactive histidine, or a pharmaceutically acceptable salt thereof.

3. The preparation according to claim 1, wherein the content of the medicine of high molecular weight is not less than 96% when analysed by HPLC, in a storage test at 50° C. for two weeks' storage, based on the value of 100% at the initial point.

4. The preparation according to claim 1, further comprising a viscous polymer.

5. The preparation according to claim 4, wherein the viscous polymer is hydroxypropyl methylcellulose.

6. The preparation according to claim 1, wherein the medicine of high molecular weight is bioactive peptide or protein.

7. The preparation according to claim 6, wherein the bioactive peptide or protein is a granulocyte colony-stimulating factor.

8. The preparation according to claim 1, wherein the preparation is adapted for intranasal administration.

9. The preparation according to claim 1, further comprising an excipient.

10. The preparation of claim 1, wherein the effective amount of the basic amino acid or its salt or derivative thereof is from 0.1 to 10.0 W/W %.

11. The preparation of claim 1, wherein the effective amount of the basic amino acid or its salt or derivative thereof is from 0.5 to 5.0 W/W %.

* * * * *